United States Patent [19]

Merrill

[11] 4,055,682

[45] Oct. 25, 1977

[54] CATHETER AND THE METHOD OF MAKING

[75] Inventor: Edward Wilson Merrill, Cambridge, Mass.

[73] Assignee: High Voltage Engineering Corporation, Burlington, Mass.

[21] Appl. No.: 670,422

[22] Filed: Mar. 25, 1976

Related U.S. Application Data

[63] Continuation-in-part of Ser. No. 200,560, Nov. 19, 1971, Pat. No. 3,773,871, Ser. No. 205,156, Dec. 6, 1971, Pat. No. 3,832,458, and Ser. No. 417,053, Nov. 19, 1973, abandoned.

[51] Int. Cl.² .............................................. B05D 3/06
[52] U.S. Cl. .................................. 427/2; 128/349 R; 427/44
[58] Field of Search ............... 427/36, 44, 2; 204/139; 128/260, 349

[56] References Cited

U.S. PATENT DOCUMENTS

| | | | |
|---|---|---|---|
| 3,281,263 | 10/1966 | Priesing et al. | 427/44 |
| 3,566,874 | 3/1971 | Shepherd et al. | 128/349 |
| 3,700,573 | 10/1972 | Laizier et al. | 427/44 |

FOREIGN PATENT DOCUMENTS

| | | | |
|---|---|---|---|
| 860,327 | 2/1961 | United Kingdom | 204/159.13 |

OTHER PUBLICATIONS

Yasuda et al., "Journ. Poly. Sci.", Part A, vol. 2, pp. 5093–5098 (1964).

Primary Examiner—John H. Newsome
Attorney, Agent, or Firm—Russell & Nields

[57] ABSTRACT

A silicone catheter is rendered hydrophilic by contacting it with N-vinyl pyrrolidone (NVP) in bulk or in solution and exposing the catheter and NVP to ionizing radiation at high dose rate. Penetration of the NVP beyond a thin surface layer is prevented by controlling the dose of ionizing radiation and the concentration of NVP.

2 Claims, 2 Drawing Figures

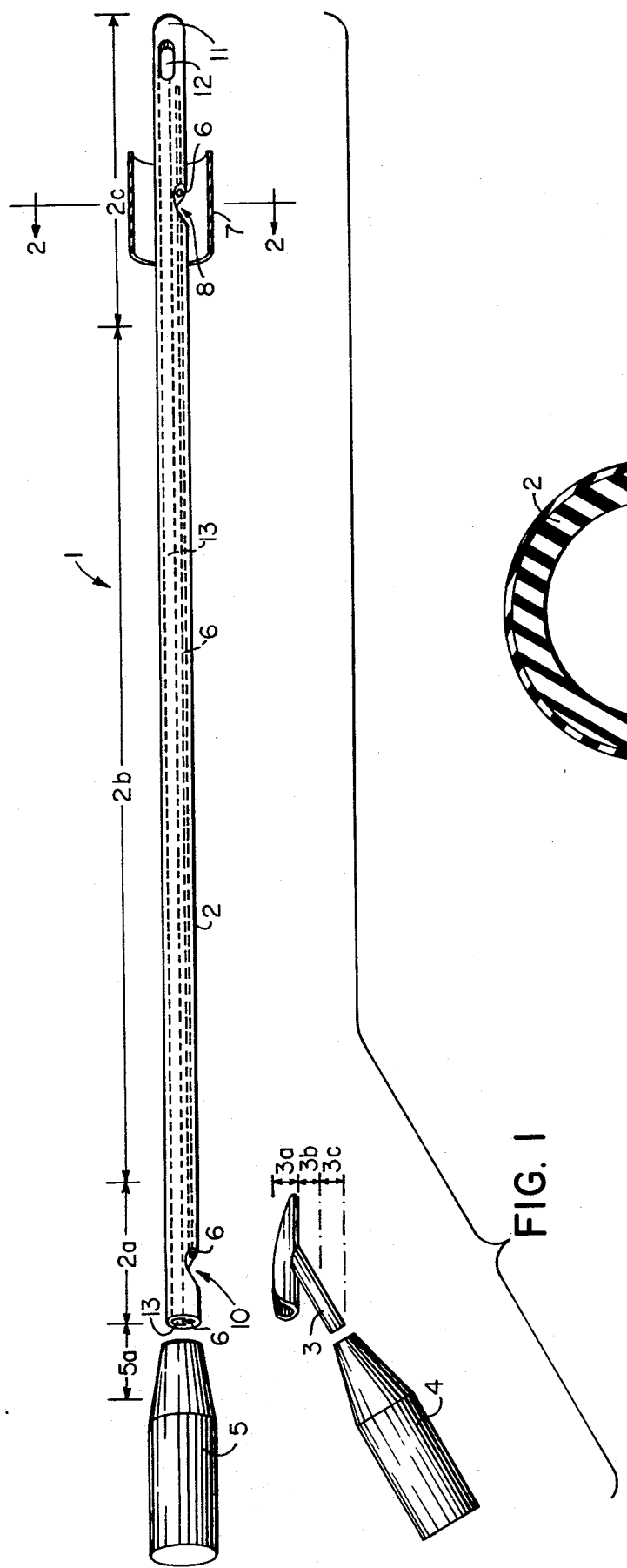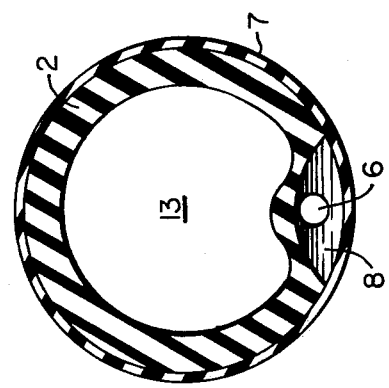

CATHETER AND THE METHOD OF MAKING

BACKGROUND OF THE INVENTION

This application is a continuation-in-part of application Ser. No. 200,560, filed Nov. 19, 1971 now U.S. Pat. No. 3,773,871, application Ser. No. 205,156, filed Dec. 6, 1971 now U.S. Pat. No. 3,832,458 and application Ser. No. 417,053, filed Nov. 19, 1973 now abandoned.

This invention relates to a process of rendering silicone catheters hydrophilic and to the catheters obtained, especially Foley catheters.

As disclosed in U.S. Pat. No. 3,566,874, the surface of a silicone catheter can be rendered hydrophilic by contacting the catheter with a hydrophilic monomer comprising a hydroxy lower alkyl acrylate or methacrylate and exposing the monomer and silicone to gamma rays to effect polymerization and grafting. However, the resultant hydrophilic layers are stiff when dry.

In an article entitled "Graft Copolymerization of Vinylpyrrolidone onto Polydimethylsiloxane", *Journal of Polymer Science*, Vol. 2, pps. 5093-5098 (1964) Yasuda et al. disclose the preparation of graft copolymers of polyvinylpyrrolidone (PVP) onto polydimethylsiloxane by a mutual irradiation technique utilizing high energy electrons for the purpose of rendering the silicone plastic hydrophilic. However, Yasuda et al. do not disclose the manufacture of catheters. Indeed, if silicone catheters are treated as disclosed by Yasuda et al. they are rendered unusable as catheters. This is because the method disclosed by Yasuda et al. for increasing hydrophilicity also changes other properties of the catheter in an undesirable way. In particular the technique disclosed by Yasuda et al. increases the stiffness of the catheter so that it becomes unusable. The lowest dose disclosed by Yasuda et al. is 1.5 megarad and the greatest dilution of the NVP disclosed by Yasuda et al. is a ratio of 80 to 20. Satisfactory catheters cannot be obtained unless either the dosage is substantially less than 1.5 megarad or the dilution of the NVP is substantially less than 80 to 20.

Midland Silicones Limited British Pat. No. 860,327 discloses the preparation of graft copolymers and in particular discloses the grafting of various monomers to silicones. There is no disclosure of the grafting of NVP to silicones. There is no disclosure of imparting hydrophilicity to silicones; the only improved properties had in the examples is the increase in tensile strength. Moreover there is no disclosure of catheters. Although at page 3 line 71 reference is made to a tube, this falls far short of a disclosure of a catheter and since none of the monomers mentioned include NVP nor is any mention made of increasing hydrophilic properties it is extremely unlikely that a catheter was intended to be included in this disclosure. As disclosed hereinafter one of the essential features of the invention is limiting the depth of grafting to a depth of approximately 10 microns while providing high concentration of grafted polymeric chains at the surface. The Midland patent clearly has nothing to do with the depth of the graft. It appears from page 4 line 122 that the samples were 1/32 of an inch and the fact that most of the examples provide irradiation with a cobalt-60 source shows that complete irradiation of the material is contemplated. Furthermore, grafting occurs when the irradiated silicone is immersed in the grafting monomer. It appears from the disclosure that the grafting monomer in which the irradiated silicones are immersed are full strength. Consequently it is clear that no effort was made to limit the penetration of the grafting monomer in the irradiated silicone.

SUMMARY OF THE INVENTION

The present invention is based upon the discovery that surface or surface layers of silicone catheters are rendered hydrophilic throughout a thin surface layer by contacting the catheter with N-vinyl pyrrolidone (NVP) monomer, in bulk or in solution and exposing the NVP and silicone to high dose rate ionizing radiation. Penetration of the NVP beyond a thin surface layer is prevented by controlling the dose and dose rate of ionizing radiation and the concentration of NVP.

BRIEF DESCRIPTION OF THE DRAWING

The drawing illustrates a catheter of the type contemplated by the invention. The coating is shown best in FIG. 2 which is a section of FIG. 1.

THE DESCRIPTIONS OF SPECIFIC EMBODIMENTS

Referring to the figures, therein is shown a catheter of the type described in my said co-pending application Ser. No. 417,053. Said catheter, generally designated as 1, is comprised of a plurality of component pieces, including a main tube 2 and a branch tube 3 having an inlet 4 associated therewith. The main tube 2 has an outlet piece 5 associated therewith. The main tube 2 has an air passageway 6 which extends throughout the length of the main tube and is formed in the wall of the main tube and is shown in FIG. 2. The catheter 1 is provided with an inflatable membrane 7, which is sealed around air outlets 8. For convenience, the membrane 7 is shown in FIG. 1 spaced apart from the tube 2. It is to be understood that, during use, the membrane 7 is adhered to the tube 2. Membrane 7 is inflated by means of air being introduced through inlet 4 and branch tube 3, air inlet 10 and air passage 6. The inlet portion 11 of the catheter 1 is provided with opposed inlet ports 12 to remove fluid from the body through passage 13 and through outlet 5.

The catheter 1 is formed by subjecting each component piece to ionizing radiation which varies along the length of the component piece. The dosage of ionizing radiation can be varied easily be selectively shielding and exposing portions of the component piece with respect to the source of ionizing radiation. For example, with reference to the main tube 2, the portion 2a, can be shielded from the source of ionizing radiation so that it is subjected to a negligible dose so that little or no crosslinking takes place. In contrast, portion 2b is subjected to a relatively high dose of ionizing radiation such as up to 20 megarads so that it is crosslinked to be mechanically stable. On the other hand, the portion 2c is subjected to an intermediate dosage of ionizing radiation such as about 0.5 to 3 megarads thereby rendering it relatively soft and pliant but mechanically strong and so that the inflatable membrane 8 is adhered to and crosslinked with the silicone in main tube 2. Similarly, portion 3a of side tube 3 and portion 5a of outlet 5 are shielded from the source of ionizing radiation so that it is subjected to none or a relatively low radiation dose, while portion 3b is subjected to a high dose of ionizing radiation to render it crosslinked and relatively hard. Portion 3c, like portion 3a, is shielded from the source of ionizing radiation so that subsequently when it is desired to join components 2, 3, 4 and 5, portions 3a and 2a as well as 2a and 5a will intercoalesce to form a seamless joint which, upon subsequent exposure to ionizing radiation, is crosslinked to form a unitary construction. Similarly, portion 3c is inserted into an opening in component 4 to contact uncrosslinked silicone to intercoalesce therewith and form a seamless joint which, upon exposure to subsequent ionizing radiation, forms a unitary construction.

Suitable silicone polymeric material that may be used include homopolymers and interpolymers formed from difunctional disubstituted siloxanes, such as dimethyl siloxane, diethyl siloxane, vinyl methyl siloxane, vinylphenyl siloxane, methyl phenyl siloxane, and diphenyl siloxane: for example, poly [dimethyl co-vinylmethyl siloxane]poly [dimethyl co-phenylmethyl siloxane]. For best results, it is preferred to have a polymer of molecular weight 100,000 or more, containing fume silica as a reinforcing agent in an amount up to 60 weight percent. The silicone can contain other additives including pigments like titanium dioxide. Fume silica can be also usefully added to imporve the rheological characteristics of the raw polymer by imparting a yield stress so that the uncrosslinked material, after shaping, may be more readily separated from molding surfaces, and more effectively resists sag or creep until completely crosslinked.

In accordance with this invention, the surface of the catheter, formed as described above or by any other suitable process, is rendered hydrophilic. The hydrophilic surface is formed by immersing the catheter into a liquid monomer, which monomer can be grafted to the surface of the silicone to form a hydrophilic surface. The immersed catheter and monomer then are subjected to one or a few doses of ionizing radiation, totaling between 1 and 10 megarads. Generally, dose rates should be in the order of about 100,000 rads per second. Such dose rates are readily obtained with conventional electron accelerators, such as Van de Graaff accelerators, linear accelerators, etc. Upon removal from the liquid, the catheter is coated with a hydrophilic layer as evidenced by deep staining with toluidine blue and wettability by a film of water. The region where the graft has occurred becomes glossy and glass-like when dry and can be inserted into the body more readily in this condition than can the original rather tacky silicone surface.

Suitable exemplary monomers include N-vinyl pyrrolidone (NVP), a mixture of NVP and one or more hydroxy lower alkyl acrylates or methacrylates such as hydroxy ethyl methacrylate (HEMA), or aqueous solutions thereof.

It is necessary to deliver the radiation for grafting within a short time; otherwise, the monomer, especially the hydroxy-acrylates, itself becomes a gel due to crosslinking with resultant erratic attachment to the silicone surface. Accordingly, radiation sources such as cobalt-60 are not useful since the required radiation dosages are delivered over a period of hours. Satisfactory results are obtained, for example, with a dilute aqueous solution of N-vinyl pyrrolidone by immersing the silicone catheter into the solution and exposing the solution and catheter to 1.0 or more megarads from a 3-MeV Van de Graaff electron accelerator in one or more passes. It is particularly desirable to employ NVP or an NVP-containing liquid. This is because NVP is slightly soluble in silicone, unlike the hydroxy methacrylates. Upon exposure to radiation, the NVP becomes grafted to the silicone. However, in accordance with the invention the intensity and duration of radiation and the concentration of the monomer are controlled in such a way as to prevent excessive migration of precursor into the silicone polymer composition thereby causing said precursor to graft to said surface and thereby producing a thin smooth hydrophilic layer uniformly over the entire surface. This hydrophilic layer must be so thin that the stiffness of the catheter after treatment when dry is not substantially greater than that of an uncoated catheter of the same composition and degree of cross-linking. For example, the silicone may be exposed to a solution of NVP, HEMA (hydroxy ethyl methacrylate), and water, which results in a surface layer predominately the copolymer of NVP and HEMA with some invasion by the NVP into the silicone. Alternatively, a dilute solution of NVP may be employed. Pure NVP may be used as long as the dose of ionizing radiation is kept sufficiently low, preferably below 1.0 megarad.

It is to be understood that the present invention is useful with any type of available catheter such as ureteral, urethral or trachial catheter. Furthermore, it is to be understood that the above identified applications are incorporated herein by reference.

The following examples illustrate the present invention and are not intended to limit the same.

EXAMPLE 1

A silicone Foley catheter was partially immersed in a solution of 4% NVP by weight, 16% HEMA and 80% water, and submitted to a single dose of electron radiation from a 3 Mev Van de Graaff accelerator amounting to 3.5 megarad. The catheter after this treatment and rinsing was found to have a thin, nearly superficial layer, strongly absorbing toluidine blue from aqueous solution. The thickness of this coating as swollen in water was around 10 microns.

EXAMPLE 2

Six silicone Foley catheters were exposed to high-energy electron irradiation from a 3 MeV Van de Graaff accelerator to a total dose of 1.5 megarad. Three were so exposed under conditions disclosed by the prior art of said article by Yasuda et al. and the remaining three were so exposed under the preferred conditions of the present invention.

The following table gives the results. All catheters received a single dose of 1.5 megarad (the least used by Yasuda).

|  | NVP:H$_2$O by vol. | % Weight Increase* | | Stiffness |
| --- | --- | --- | --- | --- |
|  |  | Dry | Wet |  |
| Sample H-100-1 | 100:0 | 2.73 | 4.28 | too high |
| -2 | 90:10 | 2.02 | 4.34 | too high |
| -3 | 80:20 | 1.48 | 2.92 | too high |
| -4 | 40:60 | 1.23 | 2.65 | marginal |
| -5 | 30:70 | 0.70 | 1.33 | acceptable |
| -6 | 20:80 | 0.57 | 1.61 | like control |

*Weight increase 0.0728 g on 12.9gm catheter. Grafted surface area 100 cm$^2$. If density of new material is 1.0g/cm$^3$, 7.28 × 10$^{-2}$cm$^3$ has been added over 100cm$^2$ surface. This means thickness of graft = 7.28 × 10$^{-4}$cm = 7.27 microns. If, however, the grafted NVP is 50% vol of the layer, the rest being silicone polymer, then the above thickness is doubled. (to ca. 14 microns). At least an order of magnitude figure is 10$\mu$.

Stiffness was observed visually (and photographs thereof taken) by positioning the catheters with their forks held flat on a table surface at the edge thereof so that support ended just where the stem joins the fork. A seventh catheter was used as an uncoated control. It is necessary to have the catheter droopy like the control so that it can be easily inserted in the urinary canal. Only samples 5 and 6 provide this flexibility. Samples 1, 2, and 3 made according to the mildest conditions stated by Yasuda et al. produce a very stiff catheters; they would be uncomfortably stiff unless presoaked in water, and such prior soaking in water would be infeasible in most administrations. This is consistent with the figures cited in the above table on percent graft dry (only PVP copolymerized onto silicone) and wet (same when hydrated under water). A preferred dose is 1.3 megarad (slightly less than above) under 20:80 NVP:$H_2O$ so as to minimize damage to the silicone balloon. The conditions under which samples H-100-1 through 3 were exposed wreck the balloon, although this could be corrected by shielding.

I claim:

1. The process for rendering superficially hydrophilic a catheter formed from a silicone composition by forming on the surface thereof a hydrophilic polymeric layer so thin that the stiffness of the catheter after treatment when dry is not substantially greater than that of an uncoated catheter of the same composition and degree of crosslinking, which method comprises contacting the surface of the catheter uniformly with a liquid containing free-radical polymerizable precursor to said hydrophilic polymer layer, said precursor comprising N-vinylpyrrolidone (NVP), NVP and water or NVP, a hydroxalkyl acrylate and water, exposing said surface while in contact with said precursor to high rate dosage of high energy ionizing radiation sufficient to form a hydrophilic surface on said catheter, and controlling the intensity and duration of radiation and the concentration of the precursor to prevent excessive migration of precursor into the silicone polymer composition, thereby causing said precursor to graft to said surface and thereby producing a thin smooth hydrophilic layer uniformly over the entire surface.

2. The process for rendering superficially hydrophilic a catheter formed from a silicone composition by forming on the surface thereof a hydrophilic polymeric layer so thin that the stiffness of the catheter after treatment when dry is not substantially greater than that of an uncoated catheter of the same composition and degree of crosslinking, which method comprises contacting the surface of the catheter uniformly with an aqueous solution containing N-vinylpyrrolidone in a volumetric concentration of not greater than 50 vol % NVP, exposing said surface while in contact with said solution to high rate dosage of high energy ionizing radiation sufficient to form a hydrophilic surface on said catheter, and controlling the intensity and duration of the radiation to prevent excessive migration of precursor into the silicone polymer composition, thereby causing NVP to graft to said surface and thereby producing a thin smooth hydrophilic layer over the entire surface.

* * * * *